United States Patent
Blau

(10) Patent No.: US 11,253,218 B2
(45) Date of Patent: Feb. 22, 2022

(54) DEVICE FOR DETERMINING THE ANTEVERSION ANGLE

(71) Applicant: Stryker European Operations Holdings LLC, Kalamazoo, MI (US)

(72) Inventor: Arno Blau, Staufen Im Breisgau (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 120 days.

(21) Appl. No.: 16/756,628

(22) PCT Filed: Oct. 16, 2017

(86) PCT No.: PCT/IB2017/056407
§ 371 (c)(1),
(2) Date: Apr. 16, 2020

(87) PCT Pub. No.: WO2019/077388
PCT Pub. Date: Apr. 25, 2019

(65) Prior Publication Data
US 2020/0323506 A1    Oct. 15, 2020

(51) Int. Cl.
*A61B 6/00* (2006.01)
*G06T 7/73* (2017.01)
(Continued)

(52) U.S. Cl.
CPC .......... *A61B 6/505* (2013.01); *A61B 6/5217* (2013.01); *G06T 7/60* (2013.01); *G06T 7/73* (2017.01);
(Continued)

(58) Field of Classification Search
CPC ..... A61B 6/4441; A61B 6/505; A61B 6/5217; A61B 17/72; A61B 2090/067;
(Continued)

(56) References Cited

U.S. PATENT DOCUMENTS

2007/0161929 A1   7/2007  Maier
2014/0228860 A1*  8/2014  Steines ................. A61B 34/30
                                                    606/130
(Continued)

FOREIGN PATENT DOCUMENTS

EP        2801320 A1    11/2014

OTHER PUBLICATIONS

Hofstetter R et al: "Computer-Assisted Fluoroscopy-Based Reduction of Femoral Fractures and Antetorsion Correction". Computer Aided Surgery. Taylor & Francis Inc ., Philadelphia. PA. US., vol. 5. Jan. 1, 2000 (Jan. 1, 2000). pp. 311-325. XP001001432, ISSN: 1092-9088. DOI: 10.1002/1097-0150(2000)5:5<311::AID-IGS1>3.O.C0;2-J.

(Continued)

*Primary Examiner* — Nay A Maung
*Assistant Examiner* — Jose M Torres
(74) *Attorney, Agent, or Firm* — Lerner, David, Littenberg, Krumholz & Mentlik, LLP

(57) ABSTRACT

A device, a system and a method for determining an anteversion angle of a femoral shaft of a femur are provided. The device includes a provision unit and a processing unit. The provision unit is configured to provide image data of the femur, and wherein the processing unit is configured to determine a longitudinal shaft axis extending through the femoral shaft based on the image data. The processing unit is further configured to determine at least two landmarks of the femur based on the image data, and place a tangent trough each landmark parallel to the shaft axis. The processing unit is configured to determine the anteversion angle of the femoral shaft based on the tangents and the shaft axis of the femoral shaft.

8 Claims, 4 Drawing Sheets

(51) Int. Cl.
*G16H 50/30* (2018.01)
*G16H 30/40* (2018.01)
*G06T 7/60* (2017.01)
*A61B 90/00* (2016.01)

(52) U.S. Cl.
CPC ............ *G16H 30/40* (2018.01); *G16H 50/30* (2018.01); *A61B 6/4441* (2013.01); *A61B 2090/067* (2016.02); *G06T 2207/10116* (2013.01); *G06T 2207/30008* (2013.01)

(58) Field of Classification Search
CPC ..... A61B 2090/3764; G06T 7/60; G06T 7/73; G06T 2207/10116; G06T 2207/30008; G16H 30/40; G16H 50/30; A61F 2002/4668
See application file for complete search history.

(56) References Cited

U.S. PATENT DOCUMENTS

| | | | |
|---|---|---|---|
| 2016/0015465 A1* | 1/2016 | Steines | A61B 17/17 623/18.11 |
| 2016/0045317 A1* | 2/2016 | Lang | G05B 19/4099 700/98 |
| 2016/0213343 A1 | 7/2016 | Barth et al. | |
| 2018/0055655 A1* | 3/2018 | Mahfouz | A61F 2/4684 |

OTHER PUBLICATIONS

International Seach Report for PCT/IB2017/056407 dated Jun. 5, 2018.
International Preliminary Report on Patentability including Amendments under Article 34 for PCT/IB2017/056407 dated Sep. 20, 2019.

* cited by examiner

DEVICE FOR DETERMINING THE ANTEVERSION ANGLE

CROSS-REFERENCE TO RELATED APPLICATIONS

The present application is a national phase entry under 35 U.S.C. § 371 of International Application No. PCT/IB2017/056407, filed Oct. 16, 2017, published in English, the disclosure of which is incorporated herein by reference.

FIELD OF THE INVENTION

The invention relates to the field of X-ray assistance for surgery. In particular, the invention relates to a device, a system and a method for determining the anteversion angle based on two tangents through two landmarks of the femur.

BACKGROUND OF THE INVENTION

In every surgery, where intraoperative imaging is used, it is a challenge to accurately perform the necessary steps of a procedure of treating a bone fracture. Usually, almost each step requires an iterative process based on several X-ray images. A significant radiation exposure is thus produced. The amount of radiation may be highly dependent on the know-how and skill of the physician.

Some systems may provide virtual information about a current position of an implant related to a bone. Also it may be possible to provide information on how to adjust the current implant or instrument position to optimise the current procedural steps. However, the availability of this information is highly dependent on the visibility of necessary structures in the image, like a reference body, a certain anatomical structure, an aiming device, a drilling sleeve or the like.

In a case, in which a shaft of a long bone is fractured, a bone nail may be used to stabilize the parts of the bone during the healing of the fracture, wherein the bone nail may be inserted into a medullary channel of the bone in a longitudinal direction thereof. However, such a bone nail may allow a rotation of one part of the bone relative to another part of the bone about the axis of the bone nail at least until a locking screw is inserted through the bone nail in a lateral direction to fix the position of the rotatable part. An important piece of information for positioning the bone nail in view of the femur may be the anteversion angle of the femur.

Accordingly, a physician should position the fractured parts as anatomically correct as possible. One approach may be to take into account features of the healthy counterpart of the fractured bone to provide information as to how the parts of the fractured bone should be arranged.

SUMMARY OF THE INVENTION

It may be seen as an object of the invention to provide a device, a system and a method for determining the anteversion angle of a femoral shaft of a femur. It would be of high benefit to reduce the amount of radiation to which a patient is exposed during the determination of the anteversion angle and to have a more efficient way to directly evaluate the anteversion angle of the femur.

The mentioned objects are solved by the subject-matter of each of the independent claims. Further embodiments are described in the respective dependent claims.

In accordance with the invention, a device, a system and a method for determining an anteversion angle of a femoral shaft of a femur is provided. The device comprises a provision unit and a processing unit. The provision unit is configured to provide image data of the femur. The processing unit is configured to determine a longitudinal shaft axis extending through the femoral shaft based on the image data. The processing unit is further configured to determine at least two landmarks of the femur based on the image data, wherein the processing unit is configured to place a tangent trough each landmark parallel to the shaft axis. The processing unit is configured to determine the anteversion angle of the femoral shaft based on the tangents and the axis of the femoral shaft.

In other words, the device according to the invention may be able to determine the anteversion angle of the femur based on one distal image. For doing so, the device may determine the axis of the femoral shaft. Further, the device may place two tangents through two landmarks of a femur, which are parallel to each other and parallel to the determined axis of the femoral shaft. The device may comprise the provision unit for providing the image data and the processing unit to evaluate and/or analyse the provided image data for determining the anteversion angle of the femoral shaft. The distal image data and/or the distal image of the femur may be acquired in a lateral position in view of the femur. It should be understood that the image data provided by the provision unit may comprise at least two proximal 2D images and at least one distal 2D image of the femur and/or parts of the femur.

The device, system and method described herein are not only applicable to the femur. In contrast, the determination of the anteversion angle could also be applied to any other bone, for example a bone in an arm or leg, in particular, a long bone, like the tibia or the brachium. It should be noted that such a determination of a landmark may be performed based on gray scale image data, which may be provided for example from an X-ray imaging unit, but is not limited thereto. For example, also magnetic resonance imaging can be used for providing image data.

As used herein, the term "landmark" may be an "anatomical landmark" and may refer to anything at a bone, e.g. the femur, and in particular to a geometrical aspect of a bone, i.e. a point, a line, an arc, a centre point, an axis, a cylinder surface, a ball surface, or the like. For example, a geometrical aspect of a femur may be the outer surface of the femur head, a centre of the femur head, a longitudinal axis of the femoral shaft, a most distal point on the bone surface, a line defined by the centre points of the condyles, or a line defined by the most posterior points at the condyles. It will be understood that other bones provide other and/or comparable suitable geometrical aspects. The bone or the type of the bone can be determined based on the landmark, as the landmark can be characteristic for each bone.

As used herein, the term "landmark" may encompass any feature of an implant being already inserted into a bone or at least fixedly connected to a bone, said landmark being suitable for determining a geometrical aspect as mentioned above.

As used herein, the term "tangent" refers to a straight line, which touches a trajectory, such as the landmark, only in one single point and does not intersect with said trajectory.

The device may further comprise a display unit, such as a monitor, to display the provided image data. The displayed image data may comprise the placed tangents through the landmarks as well as the determined anteversion angle of the femoral shaft.

According to another embodiment of the invention, the landmarks are arranged on condyles of the femur.

Thus, the condyles of the femur can be determined as landmarks for determining the anteversion angle of the femoral shaft. The condyles may be suitable as landmarks as they are highly visible in image data, for example in an X-ray image data. Further, the condyles are visible under different angles of the image data. Furthermore, the distance between the two condyles may correlate with the size of the femur head. Thus, the distance between the condyles may be estimated by knowing, determining and/or measuring the size of the femur head. The size of the femur head can be determined by two proximal 2D images of the femur and/or femur head. Typically, the image data is at hand if an implant, e.g. a bone nail, is inserted into the femur and/or the femoral shaft. To compare the image data acquired and/or provided by the provision unit and/or the imaging unit, a database can be used to store and/or archive data of femurs from different humans, for example shape, anteversion angle, distance between the condyles, size of the femur head, length and size of the femur etc.

According to a further embodiment of the invention, the processing unit is configured to determine a first landmark on a first condyle and a second landmark on a second condyle, which is different to the first condyle. In other words, the landmarks are on each one of the two condyles of the femur.

According to an embodiment of the invention, each landmark corresponds to a lowest point on each condyle, wherein the lowest point is the point of the condyle where the tangent through the lowest point has the largest possible distance from the shaft axis. Typically, the condyles are highly visible in image data of the femur. Since tissue and bone have a different transparency for X-ray radiation, the bone and the landmarks of the bone are highly visible in X-ray images. Therefore, also the lowest point of the condyles can be determined in an easy and reliable manner. The processing unit may determine the lowest point of the condyles automatically, by the means of image recognition, image processing and/or feature extraction. Thus, the processing unit can determine the landmarks of the bone, e.g. the condyles, the femur head or the shaft axis, by analysing the provided image data with image processing tools or feature extraction algorithms. The tangents placed through the lowest point of the condyles may be parallel to each other. Furthermore, the processing unit of the device may determine a distance between the two tangents in the image data. The distance may correlate with the accuracy of the anteversion angle determination. In other words, the larger the distance between the two tangents in the image data, the lower may be the accuracy of the determined anteversion angle. Therefore, it should be understood that the distance between the two condyles in the image data should not exceed a predefined threshold.

According to an embodiment of the invention, the anteversion angle is determined based on an intersection of a first plane and a second plane, wherein the first plane is defined by the two tangents and the second plane is defined by the shaft axis and a centre of a femur head of the femur. The centre of the femur head may be determined based on two proximal 2D images of the femur and/or the femur head. It should be noted that the two proximal images should be taken under different angles, such that a 3D determination of the centre of the femur head is enabled.

According to another embodiment of the invention, the processing unit is further configured to determine a distance of the tangents and to output an imaging instruction in case the distance exceeds a predefined threshold, wherein the imaging instruction is configured to obtain new image data with a smaller distance.

In other words, the processing unit may measure, calculate and/or determine the distance (perpendicular) between the two tangents in the provided image data (the 2D projection of the femur). If the distance exceeds a predefined threshold, the processing unit may request for another image data acquired from a different angle, such that the distance between the two tangents is below the predefined threshold. The threshold can be determined based on empiric data of femurs. The threshold may be for example 10 mm, 12 mm or 14 mm. Thus, the processing unit may request for a second distal image, which is more suitable for determining the anteversion angle of the femoral shaft. By doing so, the resulting error in the determination of the anteversion angle can be minimized, as the resulting error is proportional to the distance between the two tangents in the image data. Further, the lateral and the medial condyle of the femur can be unambiguously determined by a projection in a 2D image, if the 2D image was acquired under an angle distinct, substantial or significant divergent from a perpendicular in view of the femur. For example, the angle under which the image data was acquired diverges from the perpendicular by 10°, 20° or 30°. The angle might also be at least 15°.

According to another embodiment of the invention, the provision unit is configured to output an image instruction to obtain image data in which a distance between the tangents through the condyles is approximately to zero. With other words, the provided image data is not inclined in view of the femur. Since the tangents through the lateral and medial condyles lie, in this embodiment, in one sole plane, the anteversion angle of the femoral shaft can be determined accordingly. Further, the processing unit may use an iterative method to output an image instruction for acquiring image data with no substantial distance between the two tangents through the condyles to determine the anteversion angle of the femoral shaft.

According to an embodiment of the invention, the shaft axis corresponds to an axis of a bone nail and/or nail extending through the femoral shaft. In other words, also the bone nail could serve as a reference for the shaft axis. The bone nail may be highly visible in the X-ray images and therefore, the determination of the axis of the bone nail may be easier than to determine the shaft axis of the femur. In particular, the bone nail is typically implanted into the medullary channel of the femur, thus the axis of the bone nail and the shaft axis of the femoral shaft may coincide.

According to a further embodiment of the invention, the centre of a femur head is determined by at least two 2D images made with different imaging directions.

By providing two 2D images of a 3D object with different angles, the size as well as the shape of the 3D object can be determined. It may be possible to make two proximal images of the femur head, e.g. the first image as an AP image (anterior-posterior) and the second as an ML image (medio-lateral). With the two 2D images of the proximal situation, the centre of the femur head may be determined. The two tangents through the condyles may define a first plane. The centre of the femur head and the shaft axis of the femur shaft may define a second plane. The angle of intersection between the first plane and the second plane may correspond to the anteversion angle of the femoral shaft. The device according to the present invention may therefore be able to determine the anteversion angle of the femoral shaft based on only three 2D images of the femur, two proximal images and one distal image. It should be noted, that the device according to the present invention carries out automatically the method and the sole steps for determining the anteversion angle of the femoral shaft. Thus, a physician is not needed to identify the landmarks in the provided image data or to determine the anteversion angle of the femoral shaft. Typically, the two proximal images are already at hand due to the implantation of an implant, e.g. a bone nail. Thus, only one additional distal image of the femur has to be acquired and/or provided by an imaging unit and/or the provision unit to determine the anteversion angle of the femoral shaft. Therefore, the amount of radiation the patient is exposed to is greatly reduced.

In other words, the device according to the invention may be able to determine the anteversion angle of the femur based on one inclined distal image (and two proximal images). For doing so, the device may determine the axis of the femoral shaft. Further, the device may place two tangents through two landmarks of a femur, e.g. the condyles, which are parallel to each other and parallel to the determined axis of the femoral shaft. The distal image data and/or the distal image of the femur may be acquired in a lateral position in view of the femur, such that the two condyles of the femur can be seen in one sole image. The two parallel tangents through the two condyles may define the first plane. Further, the provision unit may provide two proximal images from the femur head. With these two proximal images, the centre of the femur head may be determined. Furthermore, the size of the femur head can be measured in the 3D representation, in particular, by means of a reference body. The size of the femur head may relate to the distance between the condyles of the femur, such that the distance between the two condyles can be determined by determining the size of the femur head. The correlation between the size of the femur and the distance between the condyles can be empirically determined and stored in a database with a plurality of datasets from different humans. The centre of the femur and the axis of the femoral shaft may define the second plane. The angle of intersection between the first plane and the second plane may correlate with the anteversion angle of the femoral shaft. Thus, the anteversion angle of the femoral shaft can be determined by only two proximal 2D images and one distal 2D image of the femur and/or parts of the femur.

Further, the distance between the two tangents in the provided image can be determined. If said distance exceeds a predefined threshold, the provision unit may acquire another distal image of the femur. Furthermore, it may be possible to minimize the distance between the two tangents in the provided image data to reduce the resulting error.

According to yet another embodiment of the invention, the image data show a reference body, which is configured to enable a 3D position determination of the reference body and therefore of the femur.

It will be understood that a 3D image, i.e. a volume image, may be generated from a stack of 2D image data and/or images oriented in one direction or based on a plurality of 2D projection images generated from different imaging angles. The reference body may be useful to determine the angle of the image in view of the femur. Further, the reference body may help to determine the size of the femur, as well as distances between characteristic portions of the femur and/or the landmarks, e.g. the two condyles of the femur.

It should be noted that the reference body may be fixedly connected to the femur and/or to an implant. As used herein, the term "fixedly connected" encompasses a direct or an indirect connection of an element to another element. For example, a reference body may be directly attached at an implant or may be indirectly coupled to an implant with, for example, an aiming device between the reference body and the implant. On the other hand, a reference body, which is integrated into an implant, i.e. which can be considered as fixedly connected to the implant, may be considered as being indirectly coupled to a bone, i.e. via the implant.

Further, the reference body may be at least a part of an implant. In other words, an implant which is adapted to be fixed at and/or in a bone may comprise elements which can be identified in an image of the bone or at least a section of the bone so that a vector may be determined based on the identified elements. For example, the elements may define points so that two elements may define a line or an axis, or the elements may define a contour, so that a centre axis may be determined.

Furthermore, the reference body may define an axis, i.e. the implant comprises an axis and the axis of the implant represents one of the longitudinal axes of the femur. In other words, based on the reference body, an axis, a straight line, a plane and/or a vector may be determined. In case an implant is already implanted into or at a femur, a landmark of the implant may be determined instead of a landmark of the femur so that the landmark of the implant may represent a landmark of the femur.

The processing unit of the device may be further configured to identify a reference body in the provided image data and the processing unit may be configured for determining a 3D orientation, size and/or shape of the reference body based on the provided image data. Furthermore, the processing unit may be configured to determine the orientation, size and/or shape of the femur based on the determined orientation, size and/or shape of the reference body.

It should be noted that the processing unit automatically carries out the steps of determining the landmarks and placing the tangents or the planes through the landmarks. For doing so, the processing unit can analyse the provided image data with image recognition, image processing or feature extraction algorithms. Alternatively or in addition the device may further comprise input means for manually identifying geometrical aspects of a bone in an image, such that the physician can manually place or define landmarks in the image data. Such input device may be for example a computer keyboard, a computer mouse or a touch screen.

According to a second aspect of the invention, a system for determining an anteversion angle of a femoral shaft of a femur is provided. The system comprises a device for determining an anteversion angle of the femoral shaft and an imaging unit. The imaging unit is configured to acquire and/or generate image data and to output the image data to a provision unit of the device for determining the anteversion angle of the femoral shaft based on the provided image data. The acquired image data may be preferably acquired under an angle distinct, substantial or significant divergent from the perpendicular in view of the femur, such that the lateral and the medial condyle of the femur can be assigned unambiguously. For example, the angle at which the image data was acquired diverges from the perpendicular over 10°, 20° or 30 in view of the femur.

In other words, the device further comprises an imaging unit for providing 2D projection image data of at least a section of the femur (proximal and/or distal). The imaging unit may be capable of acquiring images from different directions or angles. Accordingly, the imaging unit of the device may be adapted to provide 3D image data of at least a section of the femur. The imaging unit may be further configured to provide 2D projection images of the femur and/or a section of the femur with and without the reference body.

According to a further aspect, a method for determining an anteversion angle of a femoral shaft of a femur comprises the steps of:
- providing image data of the femur,
- determining a longitudinal shaft axis extending through the femoral shaft based on the image data,
- determining at least two landmarks of the femur based on the image data,
- placing a tangent trough each landmark parallel to the shaft axis, and
- determining the anteversion angle of the femoral shaft based on the tangents and the axis of the femoral shaft.

It has to be noted that embodiments are described with reference to different subject-matters. In particular, some embodiments are described with reference to method type claims whereas other embodiments are described with reference to apparatus type claims (device and system). However, a person skilled in the art will gather from the above and the following description that unless other notified in addition to any combination of features belonging to one type of subject-matter also any combination between features relating to different subject-matters is considered to be disclosed with this application.

The aspects defined above and further aspects, features and advantages of the present invention can also be derived from the examples of the embodiments to be described hereinafter and are explained with reference to examples of embodiments also shown in the figures, but to which the invention is not limited.

Figure 1:
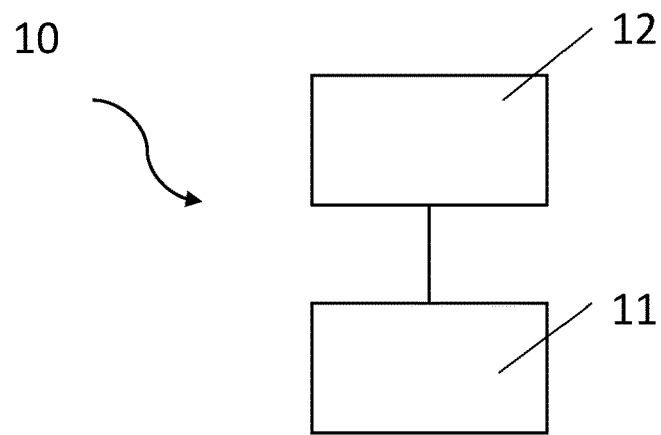
FIG. 1 shows a block diagram of a device for determining an anteversion angle of a femoral shaft.

Throughout the drawings, the same reference numerals and characters, unless otherwise stated, are used to denote similar features, elements, components, or portions of the illustrated embodiments. Moreover, while the present disclosure will now be described in detail with reference to the figures, it is done so in connection with the illustrative embodiments and is not limited by the particular embodiments illustrated in the figures.

DETAILED DESCRIPTION OF EMBODIMENTS

FIG. 1 illustrates an exemplary embodiment of a device 10 for determining the anteversion angle of a femoral shaft. The device 10 comprises a processing unit 11 and a provision unit 12. The provision unit 12 is configured to provide image data of the femur of which the anteversion angle should be determined. The processing unit 11 is configured to determine a longitudinal shaft axis through the femoral shaft based on the provided image data of the provision unit 12. The processing unit 11 further is configured to determine at least two landmarks of the femur and to place tangents through each one of the landmarks. The landmarks may be the condyles and/or the lowest point of the condyles. The processing unit 11 may determine the landmarks, e.g. the lowest point of the condyles, the femur head and/or the shaft axis through the femoral shaft, automatically, by the means of image recognition, image processing and/or feature extraction. Thus, the processing unit 11 analyses the provided image data with image processing or feature extraction algorithms. Further, the processing unit 11 is not only configured to determine geographical features of the bone, but also to place, for further processing, geographical elements, such as lines, tangents, planes, points and/or centres, in the provided image data. The tangents through the landmarks and the shaft axis of the femoral shaft may be parallel. Further, the processing unit 11 may be configured to determine the anteversion angle of the femoral shaft based on the two tangents and the shaft axis. The processing unit 11 can carry out this determination of the anteversion angle of the femoral shaft by calculating the angle of intersection between a first plane, defined by the two tangents through the condyles, and a second plane, defined by the centre of the femur head and the shaft axis.

The processing unit 11 may be further configured to define a first plane, including the two tangents, and a second plane, including the shaft axis and a centre of the femur head. The angle of intersection of the first plane and the second plane corresponds to the anteversion angle of the femoral shaft. The centre of the femur head may be determined by the processing unit 11 by means of two 2D images captured from different image angles. Based on two 2D images of the femur head, a 3D model of the femur head can be calculated. In a further step, the centre of the femur head can be determined in the 3D model of the femur head by the processing unit 11.

The processing unit 11 may also be configured to determine the shaft axis of the femoral shaft based on an implant at and/or in the femur, such as a bone nail, which is highly visible in the provided image data of the provision unit 12. Since the material of the implant has a different transparency for X-ray radiation than tissue or bone, the implant may be highly visible in the provided image data of the femur. Thus, the image recognition, image processing or feature extraction algorithms of the processing unit 11 may easily identify and determine the implant. Further, the implant may serve as landmark itself, as the shape of the implant is known and the position of the implant in the femur is also known. In other words, the implant may be inside the femoral shaft, e.g. a bone nail, and therefore, the implant corresponds to the shaft axis.

Figure 2:
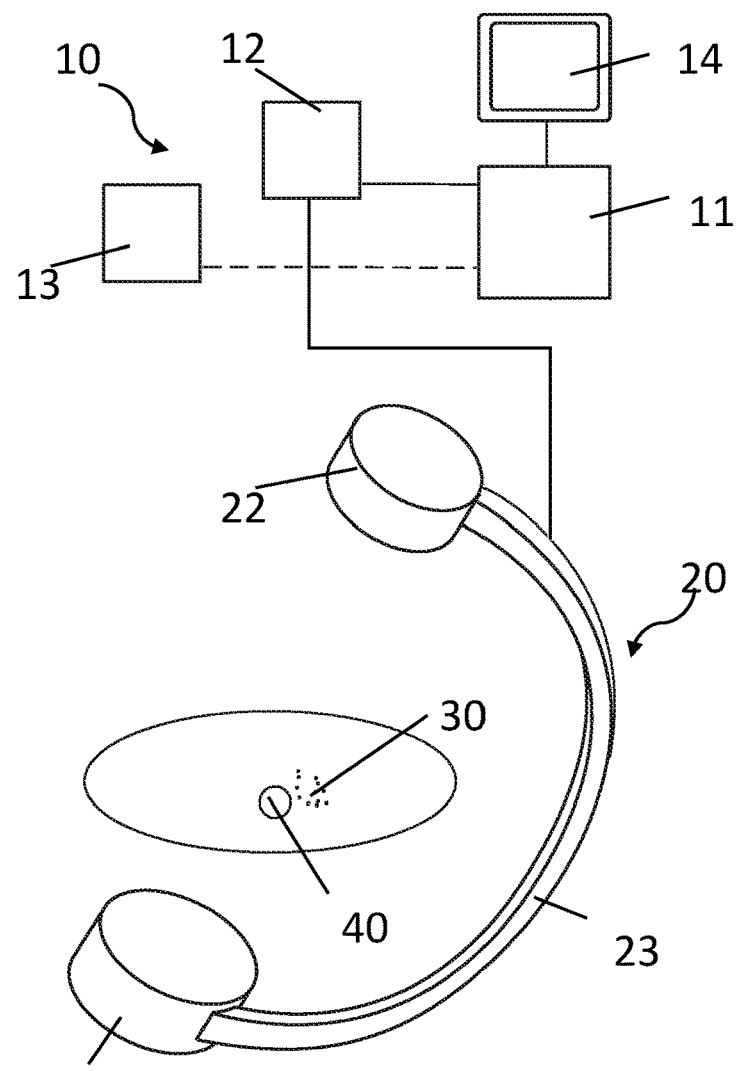
FIG. 2 shows a schematical set up for a device determining an anteversion angle of a femoral shaft with a C-arm imaging unit, a reference body and a femur according to an embodiment of the invention.

FIG. 2 shows a system for determining the anteversion angle of the femoral shaft. The system comprises the device 10 for determining the anteversion angle of the femoral shaft and an imaging unit 20 for acquiring image data of the femur and/or a reference body. In particular, the imaging unit 20 can acquire X-ray image data.

The device 10 for determining the anteversion angle of the femoral shaft, abbreviated as the device 10, may further comprise a database 13 for storing and archiving data from the imaging unit 20 and/or the device 10. The stored data in the database 13 can be compared with the data of the imaging unit 20 and/or to the device 10. Furthermore, the device 10 may comprise a display and/or monitor 14 for displaying provided image data, determined axes, planes and/or tangents.

The imaging unit 20 comprises an X-ray source 21, an X-ray detector 22 and a C-arm 23, at which the X-ray source 21 and the X-ray detector 22 are mounted. Typically, the C-arm 23 is arched, such that a probe can be placed between the X-ray source 21 and the X-ray detector 22. The probe may be the femur 40 (or a bone in general) and/or a reference body 30. The C-arm 23 can be rotated and/or moved such that image data from different angles and position can be acquired. Preferably, the C-arm 23 acquires image data under an angle distinct, substantial or significant divergent from the perpendicular in view of the femur, such that the lateral and the medial condyles of the femur can be assigned unambiguously. For example, the angle at which the image data was acquired diverges from the perpendicular over 10°, 20° or 30°. With other words, the image is generated from a substantially lateral direction but also inclined in a proximal to distal direction so that both condyles at the distal section of the femur can be identified in one image.

The imaging unit 20 may acquire image data of the femur 40 and/or the reference body 30. The imaging unit 20 further provides the acquired image data to the provision unit 12. The provision unit 12 may be a hard drive, a modem, a cloud service, a CD, a DVD, a flash drive or a memory stick.

The processing unit 11 may further determine a distance perpendicular between the two tangents in the image data, and if the distance exceeds a predefined threshold, the provision unit 12 may instruct the imaging unit 20 to acquire further image data from a different angle and/or position. The goal of the further acquired image data is to reduce the distance perpendicular between the two tangents. The threshold may be determined based on empiric data and the threshold may be for example 10 mm, 12 mm or 14 mm. Furthermore, the provision unit 12 may also be configured to provide the angle under which the further image data should be taken to the image unit 20 for acquiring image data. Further, the provision unit 12 may also provide the coordinates for the image unit 20, in respect to the femur and/or the reference body, to acquire the further image data of the femur.

The provision unit 12 may instruct the imaging unit 20 to acquire image data, in which the distance between the two tangents through the condyles is approximately zero. Thus, the provided image data is not inclined in view of the femur. Since the tangents through the lateral and medial condyle lie in one sole plane, the anteversion angle of the femoral shaft can be determined accordingly. Further, the provision unit 12 may use an iterative method to instruct the imaging unit 20 to acquire image data with no substantial distance between the two tangents through the condyles of the femur to determine the anteversion angle of the femoral shaft.

Figure 3:
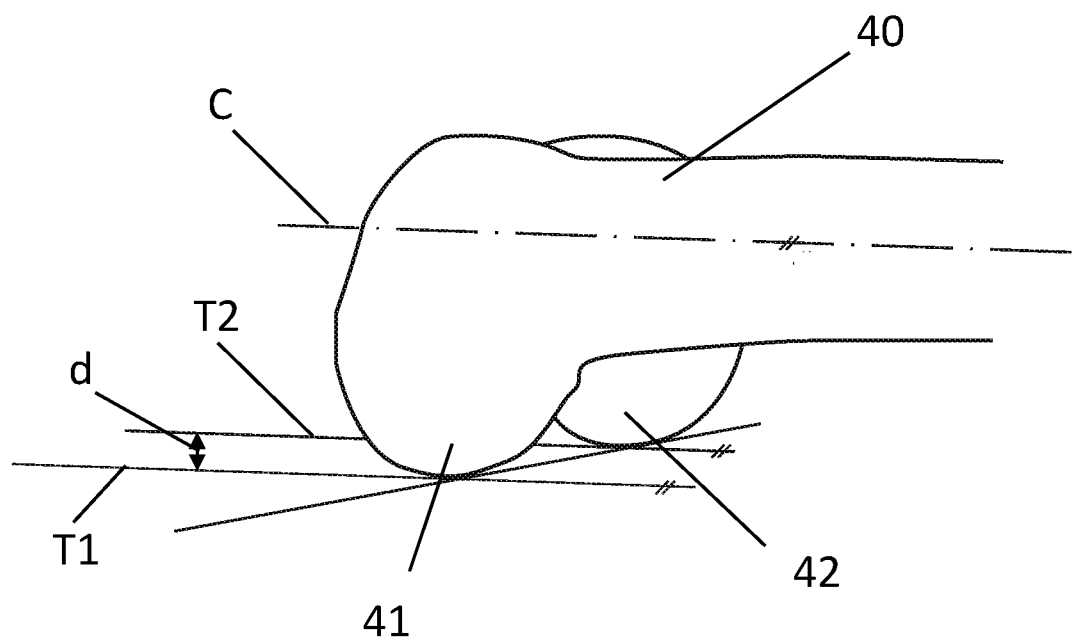
FIG. 3 shows a visualization of a distal section of a femur.

FIG. 3 shows a schematic distal image of the femur 40. The image is acquired from a predominant lateral direction, so that both condyles 41, 42 of the femur 40 are visible on the image. FIG. 3 further shows the shaft axis C through the femoral shaft, the two tangents T1, T2 as well as the projected distance d between the two tangents T1, T2. The two condyles 41, 42 were selected as landmarks of the femur 40, wherein the two tangents T1, T2 are placed through the lowest point of the condyles 41, 42, thus the point with the largest possible distance to the shaft axis C. It should be noted that the shaft axis C and the tangents T1, T2 are parallel to each other.

Figure 4:
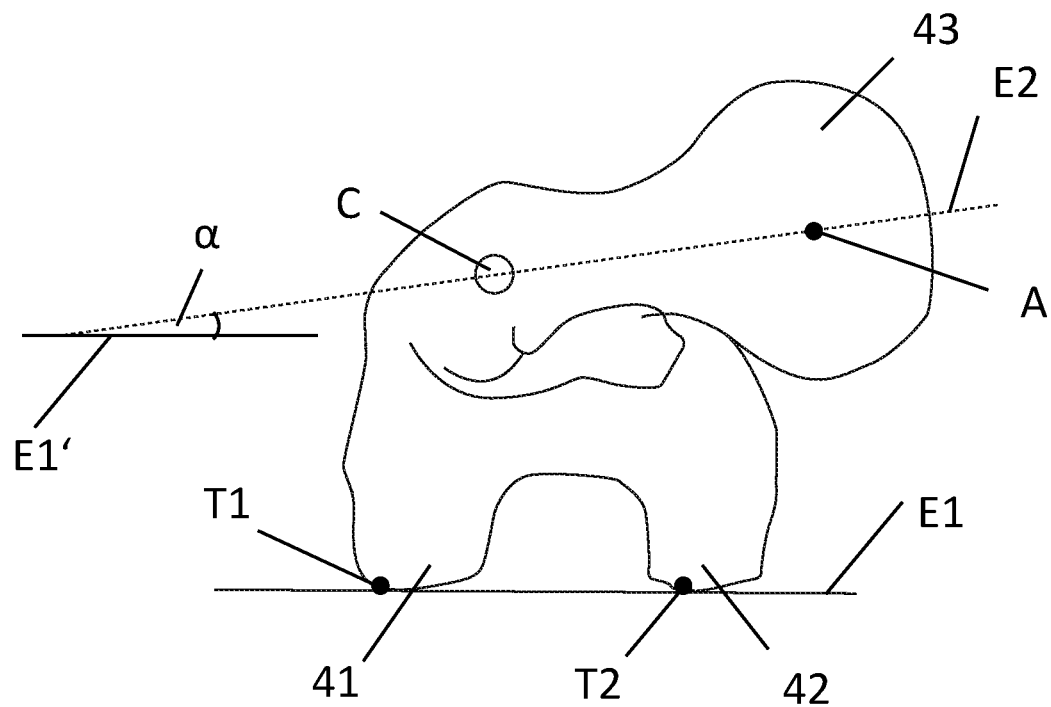
FIG. 4 shows an exemplary illustration of a femur in a proximal to distal direction.

FIG. 4 illustrates a plane view of the femur 40, i.e. the femur head 43 of the femur 40 at the proximal section as well as the condyles 41, 42 at the distal section of the femur 40. The shaft axis C as well as the tangents T1, T2 through the lowest point of the condyles 41, 42 are also shown in FIG. 4. Further, the centre of the femur head A is illustrated. The two tangents T1, T2 define a first plane E1 (illustrated by the straight line) and the centre of the femur head A and the shaft axis C define a second plane E2 (illustrated by the dotted line). The angle of intersection between the first plane E1 and the second plane E2 corresponds to the anteversion angle $\alpha$. For a better illustration of the anteversion angle $\alpha$, a third plane E1' is introduced in FIG. 4. The third plane E1' is a parallel shifted representation of the first plane E1 defined by the two tangents T1, T2.

Figure 5:
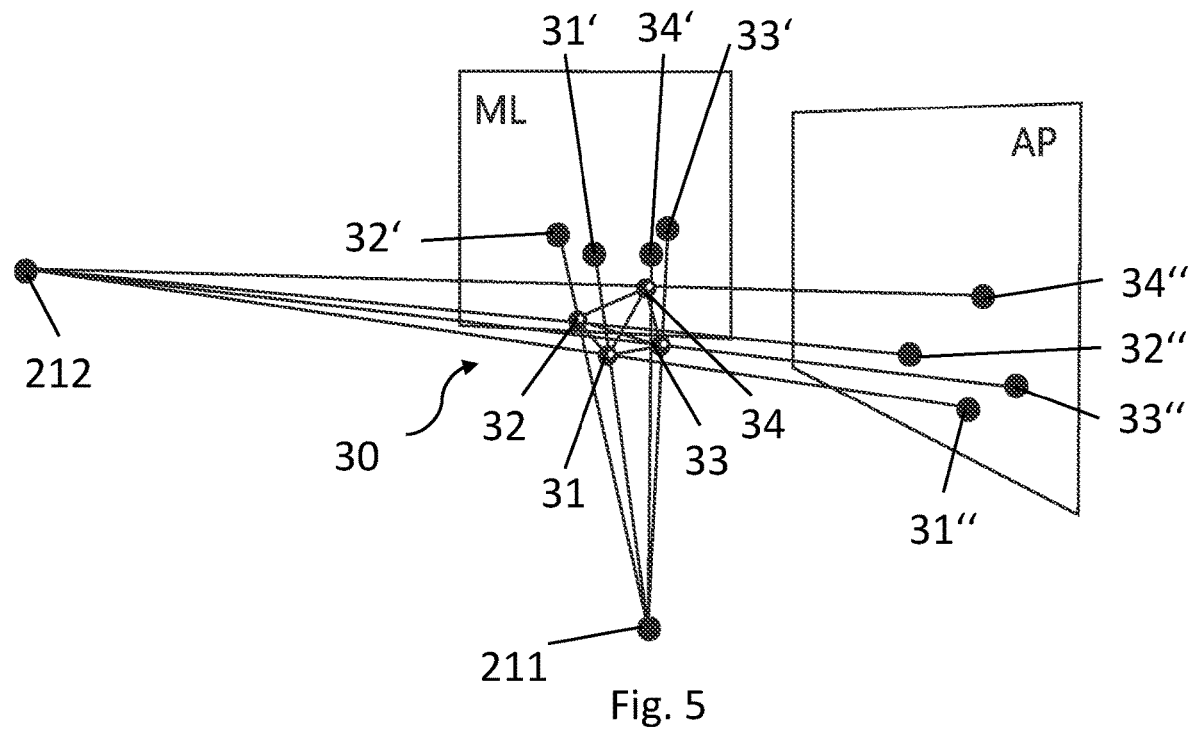
FIG. 5 shows a schematical visualization regarding a projection of a reference body.

FIG. 5 shows a reference body 30, which is formed, for example, by four spheres 31, 32, 33, 34. These spheres 31, 32, 33, 34 can be arranged in a predetermined way. Further illustrated are straight lines, which represent X-ray beams emitted by X-ray sources 211, 212, respectively. The beams ends at a projection surface named ML (medio-lateral) and AP (anterior-posterior). The spheres 31, 32, 33, 34 of the reference body 30 project a pattern on each one of the surfaces. On the ML surface, they project the pattern 31', 32', 33', 34' and in the AP surface, they project the pattern 31", 32", 33", 34". As can be seen in FIG. 5, the patterns on the two projection surfaces ML, AP differ. The design of the reference body 30 can be formed such that a unique projection pattern will apply for each projection direction. The reference body has a unique and characteristic projection in any arbitrary projection direction. Thus, it is possible to determine the 3D orientation of the reference body 30 with regard to the imaging device (the X-ray source) based on the projected images. That is, the projected images are understood by the processing unit 11 to correspond to a specific 3D orientation of the reference body 30 with regard to the imaging device. The reference body 30 may be needed to determine distances, sizes or angles in the provided image data. Furthermore, as the X-ray source is a point source, the distance between the reference body 30 and the X-ray source can be determined based on the unique pattern of the reference body 30. Alternatively, the reference body may be provided by a particular arrangement and/or pattern of fiducial markers. These fiducial markers may be radiopaque and spherical elements, which are provided on and/or inside an X-ray transparent body, the implant itself and/or the femur itself.

Figure 6:
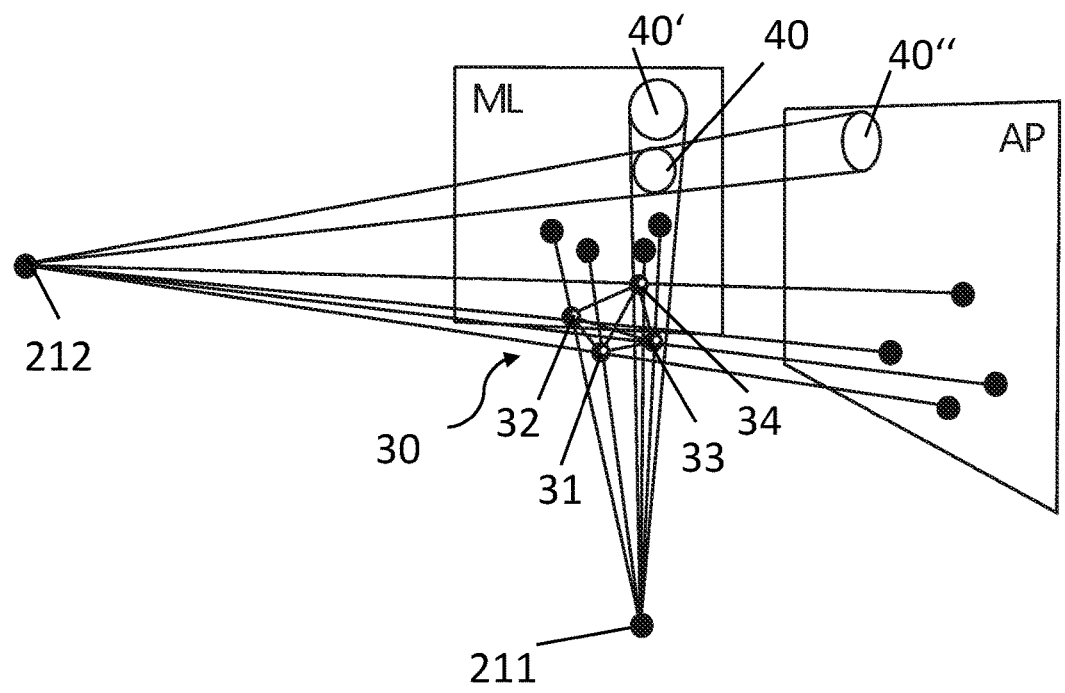
FIG. 6 shows a schematical visualization regarding a projection of a reference body with a femur.

FIG. 6 shows the arrangement according to FIG. 5 with the femur 40 next to the reference body 30. The femur 40 also is projected 40', 40" to the projection surfaces ML, AP, respectively. Since the 3D orientation and the size of the reference body 30 can be determined, also the orientation and size of the femur 40 can be determined. This can be accomplished by image recognition, image processing or feature extraction algorithms of the processing unit, i.e. by comparing the known size, orientation and shape of the reference body 30 to the femur in the provided image data.

Figure 7:
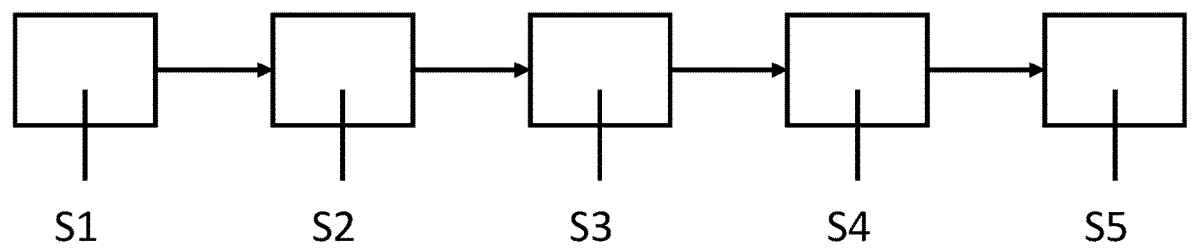
FIG. 7 shows a flow chart of steps for the method according to an embodiment of the invention.

The flow-chart in FIG. 7 illustrates the principle of the steps of the method performed in accordance with an embodiment of the invention. It will be understood that the steps described, are major steps of the method, wherein these major steps might be differentiated or divided into several sub-steps. Further, there might be sub-steps between these major steps.

In step S1, a provision unit 12 provides image data of a femur 40. The image data may comprise a complete image of the femur 40 or just a portion of the femur 40. For example, the image data provided may be a proximal and/or a distal image of the femur 40 and/or a part of the femur 40.

The provision unit 12 might be coupled to an imaging unit 20, which is configured to acquire image data, in particular 2D images, of the femur 40. The provided image data may be X-ray images of a C-arm 23 X-ray imaging unit. Further, the images provided by the provision unit 12 comprise a projection of a reference body 30, wherein the projection of the reference body 30 in the provided 2D images allows a determination of the 3D orientation of the reference body 30 and therefore also the determination of the 3D orientation of the femur 40. Therefore, the reference body has a unique and characteristic projection in any arbitrary projection direction. The unique projection can be achieved, for example, when designing the reference body 30 in a certain shape, which is visible or the projection of it is visible when being imaged. Based on the pattern and/or distances of the projected markers in the image data, the actual orientation of the reference body 30 may be determined in view of the orientation and/or direction of the provided image data.

In step S2, a longitudinal shaft axis C extending through the femoral shaft is determined based on the provided image data. The processing unit 11 determines the femur 40 and/or the femoral shaft in the provided image data by the means of image recognition, image processing or feature extraction. Furthermore, the processing unit 11 determines the axis C through the femoral shaft based on the provided image data. The shaft axis C of the femur 40 may also be determined by using a bone nail as a reference, as the bone nail is highly visible in the provided image data.

It will be understood that a single image may be sufficient to determine a landmark of the femur 40 like the shaft axis and/or the condyles 41, 42.

In step S3, at least two landmarks of the femur 40 are determined based on the provided image data of the femur 40. For example, the landmarks of the femur 40 are the condyles 41, 42. In particular, the landmarks are the lowest points of the condyles 41, 42 of the femur. As used herein, the term "lowest point" of the condyles 41, 42 refers to the point with the largest possible distance to the shaft axis of the femoral shaft.

In step S4, a tangent T1, T2 is placed through each one of the determined landmarks. The placed tangents T1, T2 are parallel to the determined shaft axis C. In particular, the tangents T1, T2 are placed through the lowest point of each one of the condyles 41, 42 of the femur 40.

In step S5, an anteversion angle α is determined including the two tangents T1, T2 and on the shaft axis. The two tangents T1, T2 may define a first plane E1 and the shaft axis C with a centre of the femur head A may define a second plane E2. The angle of intersection between the first plane E1 and the second plane E2 may correspond to the anteversion angle α of the femoral shaft.

A sub-step of the provided method may be to display the provided image data of the femur 40 and/or a part of the femur 40 with and/or without the placed tangents T1, T2 on a display or a monitor 14.

A further sub-step of the method may also be to acquire and/or to generate additional image data of the femur 40, if the projected distance d in the image data perpendicular between the two tangents T1, T2 exceeds a predefined threshold. The method further provides that the processing unit 11 can instruct the imaging unit 20 to acquire image data from a different angle and the coordinates for the imagining unit 20 for acquiring the images under this different angle. Thus, the method provides to change the position and/or the orientation of the imaging unit with respect to the femur 40 and to acquire additional image data of the femur 40.

It will be understood that the method according to an embodiment of the invention can also be applied on other anatomical structures and/or bones.

Other variations to the disclosed embodiments can be understood and effected by those skilled in the art in practising the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims.

The mere fact that certain measures are recited and mutually different dependent claims does not indicate that a combination of these measures cannot be used to advantage. Any reference signs in the claims should not be construed as limiting the scope.

LIST OF REFERENCE SIGNS 10 device for determining anteversion angle of a femoral shaft
11 processing unit
12 provision unit
13 database
14 display/monitor
20 imaging unit
21 X-ray source
22 X-ray detector
23 C-arm
30 reference body
40 femur/anatomical structure/bone
41 first condyle
42 second condyle
43 femur head
A centre of the femur head
C shaft axis of the femoral shaft
E1 plane defined by the two tangents
E1' shift of plane E1
E2 plane defined by shaft axis of the femoral shaft and centre of the femur head
d projected distance between the two tangents
T1 first tangent
T2 second tangent
α anteversion angle of the femoral shaft

The invention claimed is:

1. A device for determining an anteversion angle of a femoral shaft of a femur, comprising:
a provision unit, and
a processing unit,
wherein the provision unit is configured to provide image data of the femur,
wherein the processing unit is configured to determine a longitudinal shaft axis extending through the femoral shaft based on the image data,
wherein the processing unit is further configured to determine at least two landmarks of the femur based on the image data,
wherein each landmark corresponds to a lowest point on each condyle, wherein the lowest point is the point of the condyle where the tangent through the lowest point has the largest possible distance from the shaft axis,
wherein the processing unit is further configured to place a tangent through each landmark parallel to the shaft axis, and
wherein the processing unit is configured to determine the anteversion angle of the femoral shaft based on the tangents and the shaft axis of the femoral shaft, wherein the anteversion angle is determined based on an intersection of a first plane and a second plane, wherein the first plane is defined by the tangents and the second plane is defined by the shaft axis and a centre of a femur head of the femur, and wherein the processing unit is further configured to determine a distance perpendicular between the tangents and to output an imaging instruction in case the distance exceeds a predefined threshold, wherein the imaging instruction is configured to obtain new image data.

2. The device according to claim 1, wherein the landmarks are arranged on condyles of the femur.

3. The device according to claim 2, wherein the processing unit is configured to determine a first landmark on a first condyle and a second landmark on a second condyle different to the first condyle.

4. The device according to claim 1, wherein the shaft axis corresponds to an axis of a nail extending through the femoral shaft.

5. The device according to claim 1, wherein the centre of the femur head is determined by at least two 2D images made with different imaging directions.

6. The device according to claim 1, wherein the image data show a reference body, which is configured to enable a 3D position determination of the reference body and of the femur.

7. A system for determining an anteversion angle of a femoral shaft of a femur, comprising:

the device according to claim 1, and an imaging unit, wherein the imaging unit is configured to generate image data and to output the image data to the provision unit of the device for determining the anteversion angle of the femoral shaft.

8. A method for determining the anteversion angle of a femoral shaft of a femur comprising the steps of:

providing image data of the femur, determining a longitudinal shaft axis extending through the femoral shaft based on the image data, determining at least two landmarks of the femur based on the image data, wherein each landmark corresponds to a lowest point on each condyle, wherein the lowest point is the point of the condyle where the tangent through the lowest point has the largest possible distance from the shaft axis, placing a tangent through each landmark parallel to the shaft axis, and determining the anteversion angle of the femoral shaft based on the tangents and the shaft axis of the femoral shaft, wherein the anteversion angle is determined based on an intersection of a first plane and a second plane, wherein the first plane is defined by the tangents and the second plane is defined by the shaft axis and a centre of a femur head of the femur, and determining a distance perpendicular between the tangents and outputting an imaging instruction in case the distance exceeds a predefined threshold, wherein the imaging instruction is configured to obtain new image data.

* * * * *